United States Patent
Krupa et al.

(10) Patent No.: US 8,193,405 B2
(45) Date of Patent: *Jun. 5, 2012

(54) METATHESIS UNIT PRETREATMENT PROCESS WITH FORMATION OF OCTENE

(75) Inventors: Steven L. Krupa, Fox River Grove, IL (US); Jill M. Meister, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 428 days.

This patent is subject to a terminal disclaimer.

(21) Appl. No.: 12/552,682

(22) Filed: Sep. 2, 2009

(65) Prior Publication Data

US 2009/0326295 A1 Dec. 31, 2009

Related U.S. Application Data

(62) Division of application No. 12/263,879, filed on Nov. 3, 2008, now Pat. No. 7,601,309, which is a division of application No. 11/283,353, filed on Nov. 18, 2005, now Pat. No. 7,459,593.

(51) Int. Cl.
C07C 7/04 (2006.01)
(52) U.S. Cl. .......... 585/809; 585/802; 585/807
(58) Field of Classification Search .................. None
See application file for complete search history.

(56) References Cited

U.S. PATENT DOCUMENTS 5,877,372 A * 3/1999 Evans et al. .......... 585/510
2004/0267067 A1 * 12/2004 Bridges et al. .......... 585/324

* cited by examiner

Primary Examiner — Tam M Nguyen
(74) Attorney, Agent, or Firm — Maryann Maas

(57) ABSTRACT

Disclosed is a process for integrating a butene dimerization process with a metathesis process to remove isobutene from the feed stream to the metathesis reactor. The isobutene is preferentially dimerized in the dimerization process to leave n-butenes for metathesis with ethylene. An upstream selective hydrogenation process also isomerizes 1-butenes to 2-butenes which is the preferred butene reagent in the metathesis process. A common fractionator column for the dimerization and hydrogenation processes is also described.

5 Claims, 1 Drawing Sheet

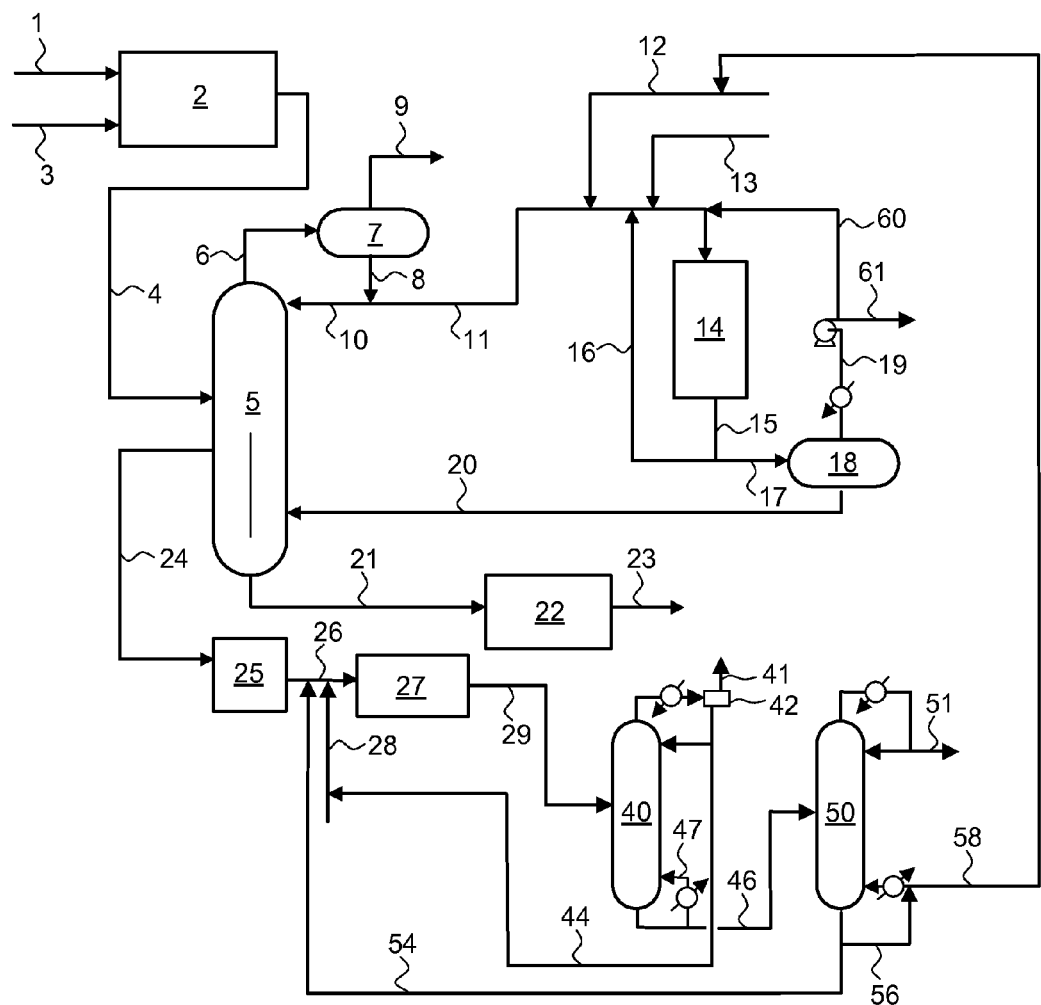

METATHESIS UNIT PRETREATMENT PROCESS WITH FORMATION OF OCTENE

CROSS-REFERENCE TO RELATED APPLICATIONS

This application is a Division of application Ser. No. 12/263,879 filed Nov. 3, 2008, now U.S. Pat. No. 7,601,309, which is a Division of application Ser. No. 11/283,353 filed Nov. 18, 2005, now U.S. Pat. No. 7,459,593, the contents of which are hereby incorporated by reference in their entirety.

FIELD OF THE INVENTION

The invention is a process for converting an olefinic $C_4$ stream into propylene and octene. Specifically, the invention relates to an integrated dimerization and metathesis process.

BACKGROUND OF THE INVENTION

Steam cracking processes are used to produce ethylene and propylene as basic petrochemicals. Steam cracking processes also produce olefinic $C_4$ hydrocarbons such as butene-1, butene-2, isobutene, butynes and butadiene. The demand for these compounds as petrochemical feedstocks is less than the quantities produced, and hence various approaches have been suggested for converting surplus $C_4$ olefins into more valuable products.

One process for conversion of olefinic $C_4$ streams is to carry out metathesis with ethylene to form propylene. This is a particularly attractive process, as it gives the steam cracker operator the flexibility to adjust the ratio of ethylene to propylene that is produced in the complex. The preferred feed for a metathesis plant is a stream rich in butene-2. Isobutene, butynes and butadiene are not desirable feeds to the metathesis process as these compounds cause deactivation of the metathesis catalyst and/or higher coke make in the metathesis process. Butene-1 is not a desirable feed to the metathesis process as it will react with butene-2 to produce pentenes and with itself to produce hexenes. These compounds are low-value byproducts. Some form of pretreatment is, therefore, normally applied to the olefinic $C_4$ stream to produce a stream rich in butene-2 that can be used as a metathesis feed.

The current state-of-the-art process for removal of isobutene from a metathesis feed is to react the isobutene to form methyl tert-butyl ether (MTBE), ethyl tert-butyl ether (ETBE) or tert-butyl alcohol (TBA). These processes can be carried out at greater than 99.9% conversion of isobutene with negligible conversion of normal butenes and, hence, permits high propylene yields in the metathesis process. The phase out of MTBE as a gasoline additive has reduced the economic advantage of this conversion route and led to a need for new processes that convert isobutene into more valuable products.

An alternative process for the removal of isobutene from a metathesis plant feed is to react away the isobutene in a polymerization process. If the entire $C_4$ stream is subjected to polymerization conditions then substantial conversion of normal butenes also occurs, which reduces the overall yield of propylene. Furthermore, separation of isobutene from normal butenes is difficult as isobutene boils very close to butene-1.

As described below, various methods have been proposed for preparing a metathesis feed from an olefinic $C_4$ stream. There remains, however, a need for improving the value of the products produced from such processes and for reducing the capital and operating costs of such processes.

RELATED ART

It has been recognized in the art that an olefinic $C_4$ stream must undergo pretreatment prior to metathesis. U.S. Pat. No. 6,075,173 issued to J. Chodorge et al. teaches removal of dienes and butynes using a selective hydrogenation process in which isomerization of butene-1 to butene-2 also occurs. The product of the selective hydrogenation process is distilled to give an overhead stream rich in isobutene and butene-1 and a bottoms stream rich in butene-2 and butane. It is taught that the overhead stream can undergo isobutene polymerization and the bottoms stream can be used as a metathesis feed.

U.S. Pat. No. 6,207,115 issued to J. Chodorge et al. discloses a process in which separation of isobutene from butene-2 prior to polymerization is optional, and the entire olefinic $C_4$ stream can be subjected to polymerization conditions to react away isobutene. The patent also teaches that the olefinic $C_4$ stream may be augmented with the products from metathesis of an olefinic $C_5$ stream.

U.S. Pat. No. 6,538,168 issued to P. Schwab et al. discloses a process in which dienes and butynes are removed by extraction or selective hydrogenation, followed by removal of isobutene by polymerization, oligomerization or reaction with an alcohol to form an ether. Butene-1 and butene-2 are not separated prior to metathesis, and the resulting product contains a high fraction of $C_5$ and $C_6$ olefins as well as propylene.

U.S. Pat. No. 6,646,172 issued to P. Schwab et al. describes a process in which isobutene and butene-1 are not separated from butene-2 prior to metathesis. The resulting $C_5$ olefin products are subjected to a further metathesis step with ethylene to give additional propylene and regenerate the butenes.

U.S. Pat. No. 6,686,510 issued to D. Commereuc et al. discloses a process for pretreating a metathesis feed and forming a high purity isobutene product. The olefinic $C_4$ stream is selectively hydrogenated to remove dienes and butynes and then distilled in a reaction distillation column that incorporates a catalyst for hydroisomerization of butene-1 to butene 2.

U.S. Pat. No. 6,872,862 issued to R. Bridges et al. teaches treating the $C_4$ stream by selective hydrogenation, followed by distillation to separate the butene stream into an isobutene-rich overhead product and a butene-2-rich bottom product that is sent to a metathesis reactor. The patent teaches sending the isobutene-rich overhead stream to a skeletal isomerization process, in which isobutene is converted to normal butenes that can be recycled to the process feed, hence increasing the overall yield of propylene.

It is also known to those skilled in the art that dimerization of isobutene may be used to form an olefinic stream rich in octene that can be blended into motor gasoline. U.S. Pat. No. 4,244,806 issued to J. Le Page et al. discloses a process for forming a stream from the products of isobutene polymerization that is suitable for blending into motor gasoline. The patent notes that a polymerization reactor that is run under selective conditions for dimerization and trimerization will produce a reactor product that contains a significant amount of unreacted butenes. The patent teaches that this limitation can be overcome by subjecting the product of the polymerization reactor to distillation to recover as overhead product a stream comprising unreacted butenes and butanes that can be sent to an alkylation process.

U.S. Pat. No. 4,393,259 issued to D. Ward et al. describes a process for producing gasoline from propane or butane, in which an alkane stream is dehydrogenated to form an alkene-rich stream that is then subjected to catalytic condensation in the presence of a solid phosphoric acid (SPA) catalyst at a pressure in the range from 15 to 1200 psig and a temperature in the range from 120° to 260° C., to form dimers and trimers.

Unconverted $C_3$ and $C_4$ compounds are separated from the dimers and trimers by distillation and recycled to the dehydrogenation zone.

U.S. Pat. No. 4,469,911 issued to H. Manning discloses a process for isobutene oligomerization in the presence of a fixed bed cation exchange resin at a temperature in the range from 30° to 60° C. and a liquid hourly space velocity in the range from 2.5 to 12 $hr^{-1}$.

U.S. Pat. No. 5,895,830 issued to L. Stine et al. describes an improvement in the dimer selectivity of a butene oligomerization process that uses SPA catalyst, caused by diluting the butene feed with a heavy saturate stream comprising paraffins having a carbon number of at least 8.

U.S. Pat. No. 5,877,372 issued to T. Evans et al. discloses dimerization of isobutene in the presence of isooctane diluent and tert-butyl alcohol, over a sulfonic acid type ion exchange resin such as Amberlyst A-15, Dowex 50 or the like, at temperatures in the range 10° to 200° C. and pressures in the range of 50 to 500 psig. It is suggested that tert-butyl alcohol improves the selectivity of dimer formation and reduces the formation of trimer and higher oligomers. The amount of selectivity modifier that is suggested is at least 1 wt-% and preferably 5 to 15 wt-%.

U.S. Pat. No. 6,689,927 issued to R. Frame et al. describes a low temperature butene oligomerization process having improved selectivity for dimerization and improved selectivity for the preferred 2,4,4-trimethylpentene isomer, caused by carrying out oligomerization in the presence of an SPA catalyst at a temperature below 112° C. in the presence of a saturated hydrocarbon diluent having a carbon number of at least 6.

SUMMARY OF THE INVENTION

It has been discovered that a significant improvement in the overall performance of the metathesis feed pretreatment complex can be obtained if the olefinic $C_4$ stream is separated to give an isobutene-rich stream that is sent to a dimerization process to produce an octene product that can be used as an olefinic motor gasoline alkylate fuel.

It has further been discovered that the capital and operating costs of such a process can be substantially reduced by combining the distillation operation of the dimerization process with the distillation operation of the metathesis pretreatment process in a single distillation column.

BRIEF DESCRIPTION OF THE DRAWING

The FIGURE is a simplified process flow diagram showing a process for treatment of an olefinic $C_4$ stream to produce propylene and octene.

DETAILED DESCRIPTION OF THE INVENTION

The process of the invention is illustrated in the drawing, which is intended only to describe one embodiment of the invention and is not intended to limit either its application or scope. Referring now to the drawing, a $C_4$ stream rich in olefinic compounds is passed through a process line 1 into a selective hydrogenation process 2. A second feed stream rich in hydrogen is introduced into the selective hydrogenation process 2 through process line 3. The feed to the subject process can be any stream that is rich in $C_4$ olefinic compounds, for example a $C_4$ stream from a steam cracking process, from a catalytic cracking process, from a metathesis process, from a butane dehydrogenation process, from an ethylene dimerization process or from another refinery process that produces $C_4$ olefins. The feed may comprise butene-1, butene-2, isobutene, butadiene, butynes, isobutane, normal butane and small amounts of other hydrocarbons such as $C_2$ compounds, $C_3$ compounds, $C_5$ compounds and $C_6$ compounds. It is well known to those skilled in the art that butynes and dienes easily undergo polymerization reactions that lead to formation of coke and reduce the effectiveness of catalysts used in downstream processes. The selective hydrogenation process is therefore operated in such a manner to partially hydrogenate butynes and butadiene to form mainly butene-1 and butene-2, without substantially converting butenes into butanes. Suitable conditions for operation of a selective hydrogenation process are well known to those skilled in the art and are described, for example, in U.S. Pat. No. 6,166,279 and U.S. Pat. No. 6,075,173. Such conditions include passing the $C_4$ mixture in the liquid phase in the presence of hydrogen at molar ratio 0.5 to 5 moles hydrogen per mole of diolefin over a catalyst comprising at least one metal selected from the group formed by nickel, palladium and platinum, deposited on a support such as aluminum oxide, at a temperature of 200 to 200° C., a pressure of 689 to 3447 kPa(g) (100 to 500 psig), and a space velocity of 0.5 to 10 $hr^{-1}$. Two or more reaction zones may be used, and each reaction zone may employ a recycle of reactor effluent to the reactor inlet with a ratio of recycle to fresh olefinic feed stream ranging from 0 to 20. The residual butadiene content of such a process can be in the range 1 to 100 wppm, depending on the severity of the operation. The selective hydrogenation process also causes isomerization of butene-1 to butene-2, as described in U.S. Pat. No. 6,166,279. In the process of the invention, such isomerization is desirable, as it increases the overall yield of propylene from the metathesis process. The selective hydrogenation process is preferably carried out under conditions such that the ratio of butene-2 to butene-1 in the product is greater than 10, and more preferably greater than 12. The selective hydrogenation process may consist of a first reaction zone primarily for butadiene hydrogenation prior to a second reaction zone primarily for butene isomerization.

A partially hydrogenated effluent stream is withdrawn from the selective hydrogenation process 2 through process line 4 and is fed to a distillation column 5. In distillation column 5, butene-1 and compounds boiling at lower temperatures than butene-1 are removed as an overhead fraction through process line 6. The overhead fraction is sent to a partial condenser 7, where $C_4$ compounds are condensed to form an isobutene-rich liquid stream that is withdrawn through process line 8, while uncondensed hydrogen and light hydrocarbon compounds are withdrawn as a vapor product through process line 9. A portion of the isobutene-rich liquid stream is sent through process line 10 to distillation column 5 to serve as a reflux for the distillation column.

A second portion of the isobutene-rich liquid stream is sent through process line 11 and subsequently mixed with a diluent that enters through process line 12, and/or a selectivity modifier that enters through process line 13, to form a dimerization reactor feed that is then fed to a dimerization reactor 14. In accordance with the process of the invention, the dimerization reactor should be operated under conditions that favor the formation of octene, while substantially restricting the formation of dodecene and higher oligomers of isobutene. Octene is defined as an olefin consisting of eight carbon atoms, not all necessarily in a straight chain with octane defined as the saturated form of octene. Conditions for the operation of a dimerization process include passing the isobutene-rich liquid over a catalyst such as SPA or a sulfonic acid ion exchange resin such as Amberlyst A-15, A-35, A-16, A-36, Dowex 50 or the like. Several means can be used to restrict the formation of dodecene and higher oligomers of butene. These include addition of a diluent to the dimerization reactor feed stream, recycle of a portion of the dimerization reactor effluent to the dimerization reactor feed stream and addition of a selectivity modifier to the dimerization reactor feed stream. Suitable diluents include paraffinic hydrocarbon compounds selected from the group comprising propane, isobutane, normal butane, isopentane, normal pentane, octane and isooctane. Higher paraffins may be a preferred diluent if SPA is used as the oligomerization catalyst. In a preferred embodiment of the present invention, the diluent is a normal butane purge stream recovered from a metathesis process. Use of selectivity modifiers is preferred when the oligomerization catalyst is a resin catalyst. Suitable selectivity modifiers include oxygenated compounds selected from the group comprising water, tert-butyl alcohol and sec-butyl alcohol. Other oxygenates may also be present. Typically, the selectivity modifier should be about 0.1 to about 3.0 wt-% and preferably about 0.5 to about 2.5 wt-% of the fresh feed when operating with a resin catalyst.

As is known to those skilled in the art, the preferred operating conditions when an SPA catalyst is used differ from those when an ion exchange resin catalyst is used. For example, when an SPA catalyst is used, the presence of a selectivity modifier, oxygenate compound is not required and a recycle of saturated octane product is preferred. Preferred relative proportions of isobutene in the feed to the reactor for operation of the dimerization process are at least 5 wt-% and preferably at least 20 wt-%. Isobutene preferably will comprise at least 33 wt-% of the total butenes fed to the reactor. The preferred ratio of paraffinic diluent to olefins in the feed to the reactor will be about 1.5 to about 3.5 for operation with SPA catalyst. The preferred ratio of paraffinic diluent to olefins in the feed to the reactor will be about 0.5 to about 3.0 for operation of the dimerization process with a ion exchange resin catalyst. Preferably, the diluent flow rate is adjusted to maintain the isobutene concentration in the feed to the reactor to no more than 55 wt-% for operation with either SPA or resin catalyst. Preferred temperatures for operation with an SPA catalyst are in the range 40° to 260° C., and more typically in the range 75° to 230° C., while preferred temperatures for operation with an ion-exchange resin catalyst are in the temperature range 0° to 200° C., and more typically in the range 40° to 150° C. Preferred pressures for operation with an SPA catalyst are in the range 689 to 8274 kPa(g) (100 to 1200 psig), and more typically in the range 1379 to 6895 kPa(g) (200 to 1000 psig), while preferred pressures for operation with an ionic resin catalyst are in the range 345 to 3447 kPa(g) (50 to 500 psig), and more typically in the range 1379 to 2413 kPa(g) (200 to 350 psig). A preferred space velocity range for operation with SPA catalyst is about 0.5 to about 5 $hr^{-1}$ and for operation with an ion-exchange resin catalyst is 0.3 to 20 $hr^{-1}$ depending on the properties of the dimerization reactor feed such as olefin content and type.

A dimerization reactor product is withdrawn from dimerization reactor 14 through process line 15. A portion of the dimerization reactor product may be recycled to the dimerization reactor feed through process line 16. A second portion of the dimerization reactor product is passed through process line 17 to a flash drum 18, in which a $C_4$-rich vapor stream and an octene-rich liquid stream are formed. The $C_4$-rich vapor stream leaves flash drum 18 in process line 19 for further processing. A portion of vapor stream in line 19 may be recycled by line 60 to the dimerization reactor 14 after condensing and compression while the remaining stream is processed through line 61. The octene-rich liquid stream is sent through process line 20 to distillation column 5. Returning the octene-rich liquid to distillation column 5 permits the recovery of unconverted butene compounds that may be present in this stream, while at the same time obviating the use of an additional distillation column within the dimerization section of the process. The octene-rich liquid is preferably fed to distillation column 5 at a position in the distillation column that is below the position at which the partially hydrogenated effluent stream is fed to the distillation column.

In one embodiment of the invention, not illustrated in the drawing, the $C_4$-rich vapor stream that leaves flash drum 18 in process line 19 or 61, if the vapor recycle is utilized, is mixed with a second diluent stream and a second selectivity modifier stream and is sent to a second dimerization reactor to form additional octene. A portion of the second dimerization reactor product may be recycled to the second dimerization reactor feed. A second portion of the second dimerization reactor product is sent to a second flash drum, in which a second $C_4$-rich vapor stream and a second octene-rich liquid stream are formed. The second $C_4$-rich vapor stream can be sent to an additional dimerization reactor, or else can be sent for recovery of butanes. The second octene-rich liquid is combined with the first octene-rich liquid in process line 20 and is returned to distillation column 5.

A bottoms product is withdrawn from distillation column 5 through process line 21, comprising substantially all of the octene that is fed into distillation column 5 through process line 20. The recovery of octene in the bottoms product is at least 98%, preferably at least 99% and more preferably at least 99.9%. The octene product may be used as an olefinic motor gasoline blending component. The bottoms product in line 21 may be processed through an alcohol recovery process, not shown, which comprises a water wash to remove the alcohol and water from the hydrocarbon product and a distillation column to separate the water from the alcohol. Other extraction or adsorption processes may be used to separate alcohol and water from the hydrocarbon. The alcohol may then be recycled to rejoin the selectivity modifier in line 13. In one embodiment of the process, the bottoms product in line 21 with or without alcohol may be sent to a hydrogenation process unit 22, in which oxygenated hydrocarbon compounds and residual olefins are converted by hydrogenation to form a hydrogenated octane-rich product that is suitable for blending into motor gasoline and leaves the process in process line 23. Suitable conditions for operation of such a process are described in U.S. Pat. No. 6,548,721, and include contacting the bottoms product in the presence of hydrogen with a saturation catalyst comprising a metal from the top row of Group VII of the Periodic Table of the Elements and a metal from Group VI-B of the Periodic Table of the Elements, at a temperature of at least 200° C., a pressure in the range from 1724 to 4482 kPa(g) (250 to 650 psig) and a liquid hourly space velocity (LHSV) in the range from 1.5 to 15 $hr^{-1}$. Preferably, the saturation catalyst includes at least 5 to 15 wt-% molybdenum and at least 5.5 wt-% sulfur.

A mid-cut product is removed from distillation column 5 through process line 24 and is sent to a metathesis reactor guard bed 25 in which contaminants such as sulfur, oxygenated hydrocarbon compounds and nitrogen are removed by adsorption to form a contaminant-free $C_4$ metathesis process feed which exits in line 26. A supplementary $C_{4+}$ stream may be introduced to line 26 exiting from the guard bed 25. An ethylene-rich feed stream may also be introduced into line 26 through process line 28. Process line 28 preferably introduces ethylene-rich feed to process line 26 to premix reactants prior to entering reactor 27, but independent entry of line 26 into reactor 27 is contemplated. The metathesis process feed is sent through process line 26 to a metathesis reactor 27 preferably after being heated. In the metathesis reactor 27, ethylene and 2-butene produce propylene. A metathesis reactor product containing ethylene, propylene and butenes is removed from metathesis reactor 27 through process line 29.

The mid-cut product is withdrawn from distillation column 5 at a point intermediate between the points where the overhead and the bottom fractions are taken. Preferably, the mid-cut product is withdrawn from distillation column 5 at a point intermediate between the points where the partially hydrogenated effluent stream and the octene-rich liquid are fed. The point at which the mid-cut product is withdrawn is chosen so as to produce a mid-cut stream that is rich in butene-2, while maintaining a concentration of isobutene in the mid-cut that is preferably less than 1 wt-%, while also maintaining a recovery of octene in the bottoms product that is preferably greater than 98%. In one embodiment of the invention, distillation column 5 may contain a dividing wall or a partition wall, extending upwards from a point below the location at which the octene-rich liquid is fed to a point above the location at which the mid-cut is withdrawn, so as to prevent isobutene that enters with the octene-rich liquid from accumulating in the mid-cut.

Conditions for the operation of metathesis reactor 27 vary widely, but typically include contacting a mixture of ethylene and butene with a metathesis catalyst comprising at least one of halides, oxides and/or carbonyls of at least one of molybdenum, tungsten, rhenium and or magnesium on a support such as silica, alumina or silica-alumina at a temperature of from about 38° to 427° C. (100° to 800° F.), a pressure from about 1379 to 4137 kPa(g) (200 to 600 psig) and a weight hourly space velocity of about 1.0 to 100 $hr^{-1}$. Typically the metathesis catalyst comprises magnesium oxide and tungsten oxide on silica or rhenium heptoxide deposited on a gamma alumina with a rhenium content (expressed as rhenium metal) in the range of 1 to 15 wt-%.

In an embodiment, the metathesis product may be fed to a deethanizer column 40 from which an overhead product comprising ethylene and lighter gases may be withdrawn, cooled and separated in separator 42. A light vapor stream may be purged from the separator 42 in line 41. If the light vapor stream is rich in hydrogen, it may be recycled to line 3 with an appropriate purge. Part of the liquid stream is refluxed to the column 40 and the remainder rich in ethylene is recycled in line 44 to supplement ethylene feed in line 28. A bottom stream is removed and fed to a depropanizer column 50 in line 46 after a portion is reboiled and returned to the deethanizer column 40 in line 47. An overhead stream comprising propylene may be withdrawn and cooled to provide propylene product in line 51 while a portion of the overhead is refluxed to the depropanizer column 50. A bottoms product of $C_4$+ material rich in 2-butene may be withdrawn from the depropanizer in line 54 and recycled to process line 26 which feeds 2-butene to the metathesis process downstream of the guard bed 25. A portion of the bottoms stream in line 56 may be split into two streams including a reboiler stream that is reboiled and fed to the depropanizer column 50. The other stream from the split in line 58 may serve as a purge from the metathesis process and may be used to supplement diluent stream in line 12 still with an appropriate purge if necessary.

The invention claimed is:

1. A process for segregation of olefinic $C_4$ compounds from at least one feed stream containing butene-2 and at least one feed stream containing octene comprising:
    a) introducing at least one feed stream comprising isobutene, butene-1 and butene-2 into a distillation column;
    b) introducing at least one feed stream comprising octene, isobutene and isobutane into the distillation column;
    c) removing an overhead product comprising hydrogen, isobutene and butene-1 from the distillation column;
    d) removing a bottoms product comprising octene from the distillation column; and
    e) removing at least one mid-cut product comprising butene-2 from the distillation column.

2. The process according to claim 1, wherein the feed streams comprising isobutene, butene-1 and butene-2 are fed to the distillation column at positions above the positions where the feed streams comprising octene, isobutene and isobutane are fed to the distillation column.

3. The process according to claim 1, wherein the mid-cut product is removed from a location below the lowest point at which a stream comprising butene-2 is fed and above the highest point at which a stream comprising octene is fed.

4. The process according to claim 1, in which a portion of the overhead product of step (c) is sent to a dimerization reactor.

5. The process according to claim 1, in which the mid-cut product of step (e) is combined with a stream comprising ethylene and is sent to a metathesis reactor.

* * * * *